US00PP20048P3

(12) United States Plant Patent
Apps

(10) Patent No.: US PP20,048 P3
(45) Date of Patent: Jun. 2, 2009

(54) DAYLILY PLANT NAMED 'MEAN MISTER MUSTARD'

(50) Latin Name: *Hemerocallis hybrida/Daylily*
Varietal Denomination: Mean Mister Mustard

(75) Inventor: Darrel A. Apps, Wild Rose, WI (US)

(73) Assignee: Centerton Nursery, Inc., Bridgeton, NJ (US)

( * ) Notice: Subject to any disclaimer, the term of this patent is extended or adjusted under 35 U.S.C. 154(b) by 11 days.

(21) Appl. No.: 11/979,456

(22) Filed: Nov. 2, 2007

(65) Prior Publication Data

US 2009/0119815 P1 May 7, 2009

(51) Int. Cl.
*A01H 5/00* (2006.01)

(52) U.S. Cl. ..... Plt./312
(58) Field of Classification Search ..... Plt./312
See application file for complete search history.

(56) References Cited

PUBLICATIONS

Anonymous Hemercallis Mean Mister Mustard. available at http://www.whiteflowerfarm.com/31035–product.html.*

* cited by examiner

*Primary Examiner*—Wendy C. Haas
(74) *Attorney, Agent, or Firm*—Buchanan Ingersoll & Rooney PC

(57) ABSTRACT

A new and distinct *Hemerocallis* cultivar is provided. The new cultivar is very floriferous and forms attractive highly ruffled deep yellow flowers displaying a burgundy eye zone and edges, substantial substance, and a funnel-shaped form over an extended period of time. In U.S.D.A. Hardiness Zone No. 6, blooming commonly begins during late June and commonly ends during mid-August. The new cultivar displays a plurality of fans and a plurality of scapes per fan. The new cultivar is well suited for growing as distinctive colorful ornamentation in the landscape.

5 Drawing Sheets

Figure 1:
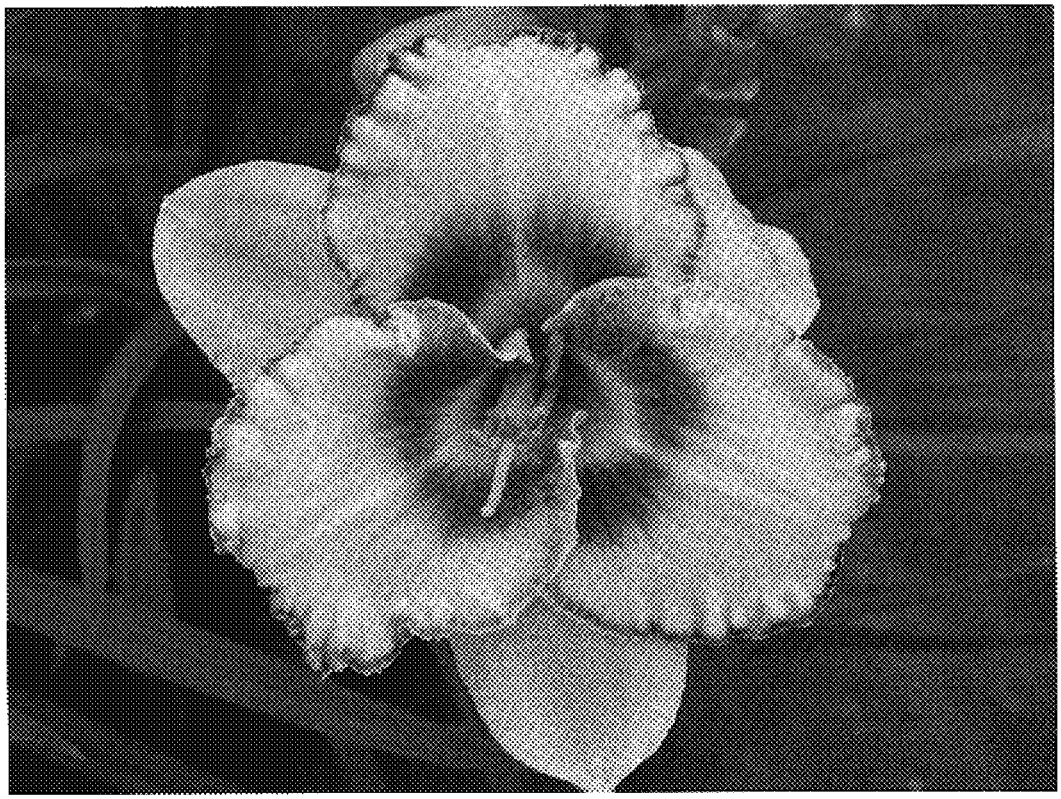

Botanical/commercial classification: *Hemerocallis hybrida*/Daylily.
Varietal denomination: cv. Mean Mister Mustard.

SUMMARY OF THE INVENTION

The present invention comprises a new and distinct cultivar of *Hemerocallis* plant of the dormant type, and hereinafter is referred to by the cultivar name 'Mean Mister Mustard'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during May, 1996, at Bridgeton, N.J., U.S.A. The female parent (i.e., the seed parent) of the new cultivar was the 'Strawberry Candy' cultivar (non-patented in the United States) which displays rich pink and red flowers having a diameter of approximately 10 cm and less than optimum substance.

The male parent (i.e., the pollen parent) of the new cultivar was the 'Barbara Keen Strout' cultivar (non-patented in the United States) which displays creamy yellow and burgundy flowers of less than optimum substance. Each of the parent plants is registered with the American *Hemerocallis* Society.

The parentage of the new cultivar of the present invention can be summarized as follows:

'Strawberry Candy'×'Barbara Keen Strout'.

The seeds resulting from the above pollination were sown and small plantlets were obtained which were physically and biologically different from each other. A number of such plants were transplanted into the field at Bridgeton, N.J., U.S.A., during June 1997. Selective study during June 1998 resulted in the identification of a single plant of the new cultivar.

It was found that the new *Hemerocallis* plant of the present invention is of the dormant type and:

(a) forms attractive highly ruffled deep yellow flowers having a burgundy eye zone and edge, substantial substance, and a funnel-shaped form, (b) possesses a long blooming season with repeat blooming, (c) exhibits a propensity to readily display a plurality of fans, and (d) readily forms a plurality of scapes per fan over the flowering season.

The 'Mean Mister Mustard' cultivar resembles some well-known cultivars, such as the 'Stella D' Oro' cultivar (non-patented in the United States) and the 'Happy Returns' cultivar (non-patented in the United States) in the sense that it commonly possesses an unusually long and substantially continuous blooming season (i.e., a multiple repeat character) of up to 75 days in U.S.D.A. Hardiness Zone No. 6. Such blooming commonly begins during late June and commonly ends during mid-August. This compares to a bloom period of less than about 30 days for over 99 percent of the hybrid Daylilies that are available in the trade.

As indicated, the 'Mean Mister Mustard' plant exhibits attractive highly ruffled deep yellow flowers bearing a burgundy eye zone and edges that readily can be distinguished from the orange-yellow flowers of the 'Stella D' Oro' cultivar and the medium yellow flowers of the 'Happy Returns' cultivar. To the best knowledge of the originator, the 'Mean Mister Mustard' cultivar is the first long and substantially reblooming Daylily having flowers that exhibit such a unique blend of multi-colored attributes.

The new cultivar can form up to 5 or more fans per year. This compares to approximately 6 to 8 fans per year for the 'Stella D' Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Aug. 15, 1998 at Bridgeton, N.J., U.S.A. At the time of such asexual reproduction the original plant of the new cultivar consisted of a clump of four fans that were phenotypically identical to each other. More specifically, the clump of the new cultivar was removed from the field and the fans were divided. It has been demonstrated that the characteristics of the new cultivar are firmly fixed and are well retained following this asexual reproduction.

The 'Mean Mister Mustard' plant has not been observed under all possible environmental conditions to date. Accordingly, it is possible that the phenotype may vary somewhat with variations in the environment, such as temperature, light, day length, contact with pesticides, etc.

The new cultivar will be marketed by the Assignee beginning in June, 2008.

BRIEF DESCRIPTION OF THE PHOTOGRAPHS

The accompanying photographs were prepared during August, and show as nearly true as it is reasonably possible to make the same in color illustrations of this character, the original plant and flower of the new cultivar of the present invention. The plant was being grown outdoors in the field at Bridgeton, N.J., U.S.A.

FIG. 1—illustrates a close view of a mature flower wherein the stamens and pistil are visible.

Figure 2:
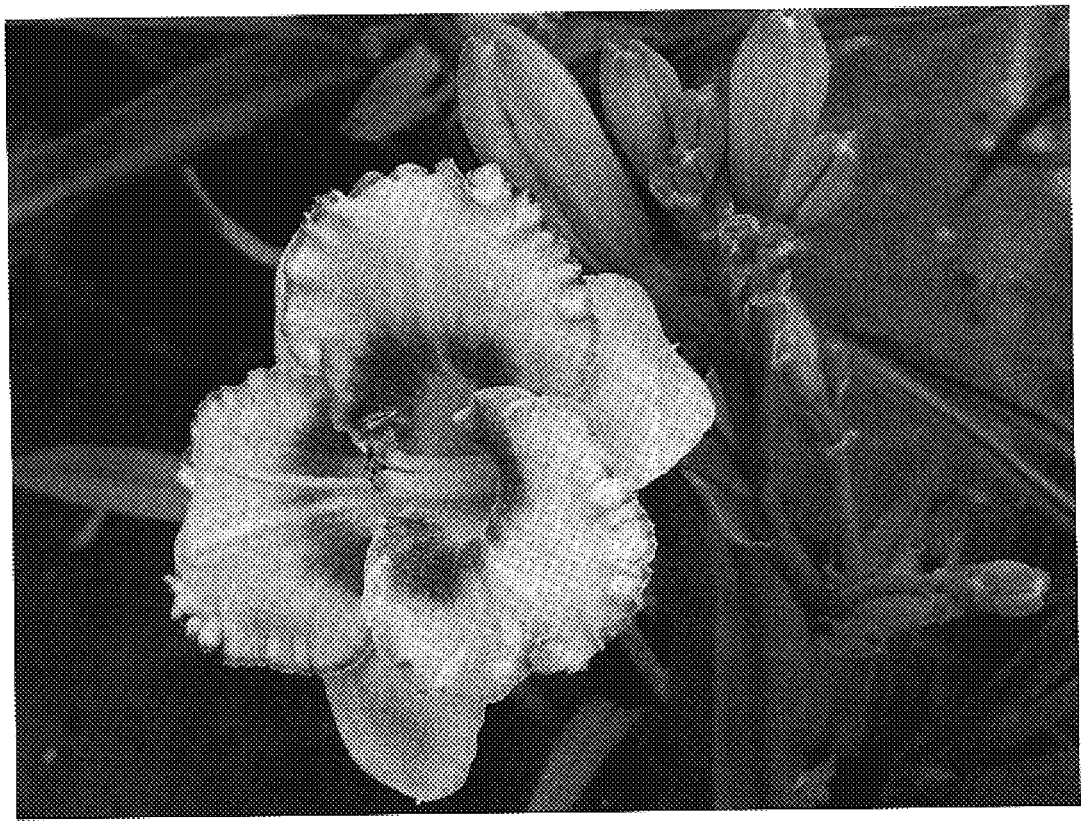

FIG. 2—illustrates a close view of a similar mature flower of the present invention wherein unopened floral buds additionally are shown.

Figure 3:
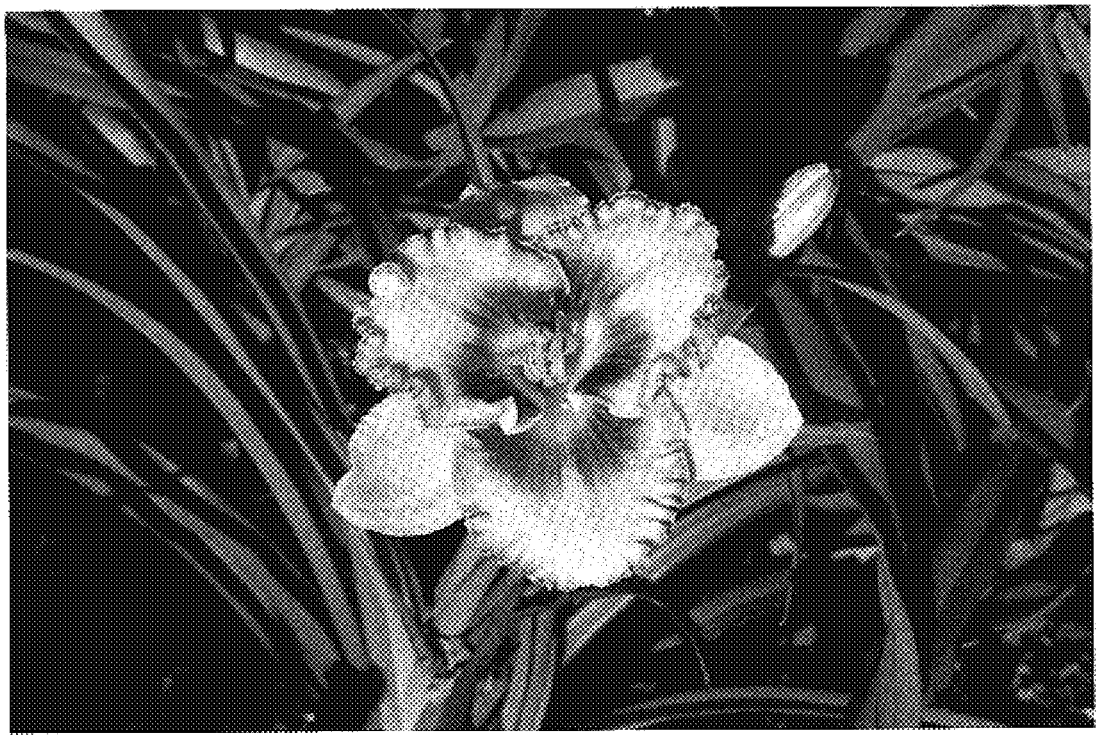

FIG. 3—illustrates a close view of a similar flower of the present invention wherein the attractive green foliage additionally is included.

Figure 4:
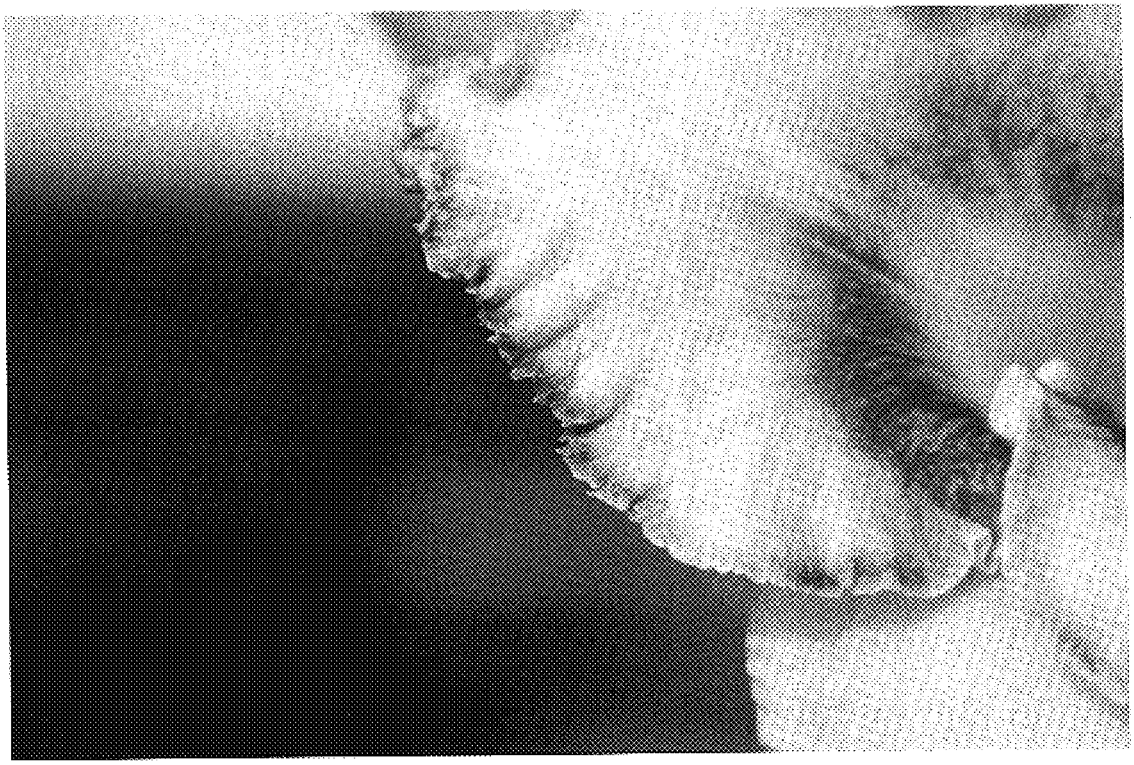

FIG. 4—illustrates a close view of a portion of an inner deep yellow tepal wherein the highly ruffled edge and burgundy coloration at the eye and edge are shown.

Figure 5:
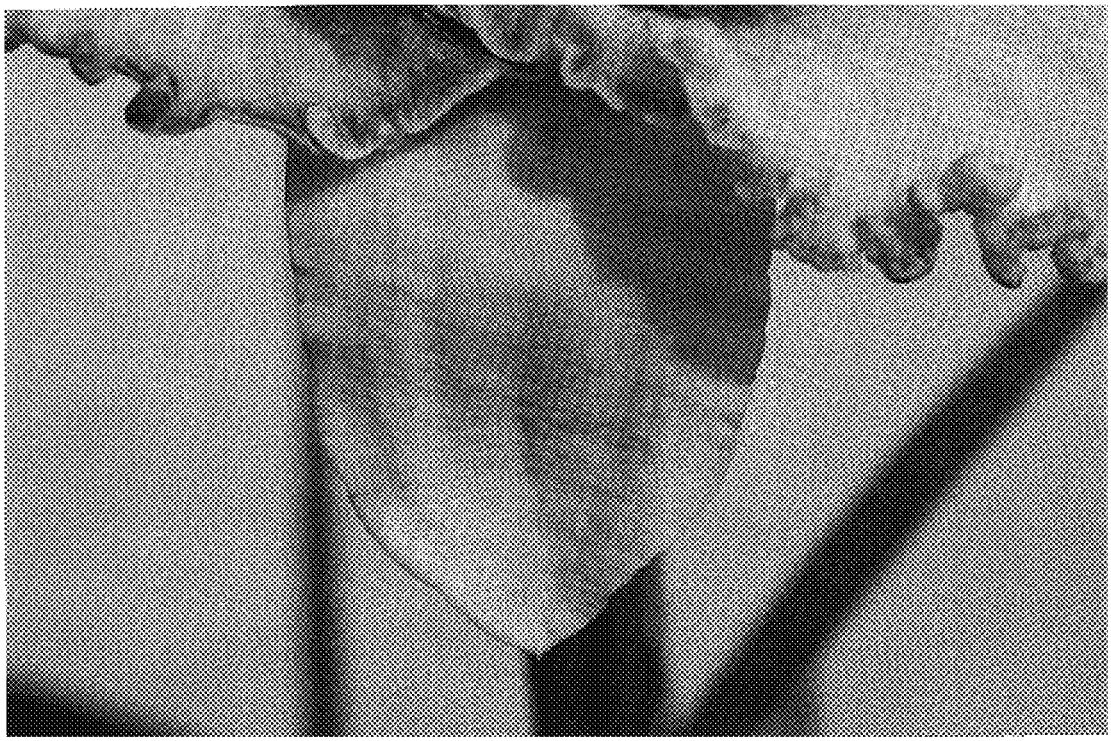

FIG. 5—illustrates at the center of photograph a close view of an outer tepal.

DETAILED DESCRIPTION

The chart used in the identification of the colors described herein is the R.H.S. Colour Chart of The Royal Horticultural Society, London, England. In some instances, more common color terms are provided and are to be accorded their usual dictionary significance. The original plant of the new cultivar is described when observed during August 2006 while growing at Bridgeton, N.J., U.S.A. under field growing conditions.

Plant:

*Height.*—Approximately 32 cm at an age of one year.

*Width.*—Approximately 74 cm at an age of one year.

*Foliage.*—Form: single stem, substantially erect fan-shaped plant having narrow arching, long, keeled, grass-like glabrous slightly textured leaves that are two-ranked at the base of the scape. Quantity: abundant, with a mature plant commonly having approximately 12 leaves per fan. Leaf Size: commonly approximately 3.5 cm in width on average and approximately 65 cm in length on average. Leaf Shape: linear and long-keeled (as illustrated in FIG. 3) with entire margins. Texture: glabrous. Color: Yellow-Green Group 146A. Type: dormant with the plant commonly retaining some green coloration during the winter in U.S.D.A. Hardiness Zone No. 6b.

*Scape.*—Color: Yellow-Green Group 147A. Length: commonly approximately 62 cm on average.

*Disease resistance.*—Typical of *Hemerocallis* with no problems having been observed to date.

Inflorescence:

*Bud.*—Form: modified oblanceolate (as illustrated in FIG. 2). Size: on the day prior to opening commonly approximately 7 cm in length on average and approximately 3 cm in width on average. Opening Rate: commonly approximately three hours on average. Peduncle Character: rigid and sturdy. Peduncle Color: Yellow-Green Group 144B.

*Flower.*—Size: commonly has a diameter of approximately 13 cm on average and a depth of approximately 8 cm on average. Borne: singly on the branchlets of a sturdy erect rachis which is ramulose. Each scape commonly has at least 20 peduncles, each of which divides into approximately 2 pedicels. Blooms Per Scape: commonly approximately 1 or 2 each day. Tepalage: each flower consists of six perianth segments wherein there are three outer tepals and three inner tepals all in an imbricated arrangement. Outer Tepal Shape: oblanceolate with slightly undulated entire margins and an acuminate apex. Outer Tepal Texture: slightly ribbed. Outer Tepal Size: commonly approximately 8.5 cm in length on average and approximately 4.5 cm in width on average. Outer Tepal Color: the overall area is Yellow-Orange Group 19A, the base is Yellow-Green Group 151C, and the eye zone is Greyed-Orange Group 173B. Outer Tepal Apex: broadly acute. Inner Tepal Shape: generally ovate. Inner Tepal Texture: pie crust ruffled edge. Inner Tepal Size: commonly approximately 7.5 cm in length on average and approximately 6.5 cm in width on average. Inner Tepal Color: the overall area is Yellow Group 12A, the base is Yellow-Green Group 151B, and eye zone and edges are Greyed-Orange Group 173A. Blooming Habit: the flowers commonly bloom substantially continuously and the scape commonly is substantially continuously in bloom for up to approximately 75 days per year in Hardiness Zone No. 6. Effects of Weather: the flowers will withstand rain damage in view of the strength of the tepals. Lasting Quality: commonly at least 16 hours. As with other *Hemerocallis* cultivars known to the inventor, the flower color eventually fades somewhat during the day with the natural effects of environmental conditions and ongoing maturity. Fragrance: none.

*Reproductive organs.*—Stamen Number: six per flower. Stamen Disposition: individually inserted at the summit of the perianth tube. Anther Disposition: introrse. Anther Size: approximately 9 mm in length.

Anther Color: Black Group 202B. Filament Configuration: slender. Filament Length: commonly approximately 5 cm on average. Filament Color: Yellow Group 6B. Pollen Color: Yellow-Orange Group 17A. Pistil Number: one per flower. Style Length: approximately 8 cm in length on average. Style Color: Yellow Group 7D. Stigma Color: Yellow Group 6C. Ovaries: three-celled, oblong, and becoming a loculiedally three-valved capsule.

*Fruit*.—Configuration: the seed pod is in the form of an ovoid capsule. Color: at maturity commonly is Yellow-Green Group 144A. Fertility: the seeds are fertile.

Hardiness: Cold tolerance is displayed in U.S.D.A. Hardiness Zone No. 5a, and heat tolerance is displayed in U.S.D.A. Hardiness Zone No. 8b.

I claim:

1. A new and distinct cultivar of *Hemerocallis* plant of the dormant type, substantially as herein shown and described, which:

(a) forms attractive highly ruffled deep yellow flowers having a burgundy eye zone and edges, substantial substance, and a funnel-shaped form, (b) possesses a long blooming season with repeat blooming, (c) exhibits a propensity to readily display a plurality of fans, and (d) readily forms a plurality of scapes per fan over the flowering season;

substantially as illustrated and described.

* * * * *